United States Patent [19]

Opel

[11] Patent Number: 4,526,178
[45] Date of Patent: Jul. 2, 1985

[54] METHOD FOR OBTAINING LACRIMAL FLUID

[76] Inventor: Helmut Opel, Hudtwalckerstrasse 2-8, 2000 Hamburg 60, Fed. Rep. of Germany

[21] Appl. No.: 551,256

[22] Filed: Nov. 14, 1983

[30] Foreign Application Priority Data

Nov. 19, 1982 [DE] Fed. Rep. of Germany ....... 3243339

[51] Int. Cl.$^3$ ............................................. B23B 31/18
[52] U.S. Cl. .................................... 128/760; 604/372; 604/294
[58] Field of Search ................ 128/760; 604/370, 372, 604/294, 297

[56] References Cited

U.S. PATENT DOCUMENTS 3,978,164  8/1976  LeBoeuf et al. ................. 604/294 X
4,329,999  5/1982  Phillips ............................... 128/760

OTHER PUBLICATIONS

Mishima, "Tear Flow Dynamics . . . ", pp. 1801–1805, pre 1979.
Phillips et al., "Long Term Sweat Collection . . . ", Jrnl. Invest. Dermatology, 68: 221–224, 1977.

*Primary Examiner*—Edward M. Coven
*Attorney, Agent, or Firm*—Roylance, Abrams, Berdo & Goodman

[57] ABSTRACT

There is described a non-irritating method for obtaining lacrimal fluid in the form of resting secretion, in which a hydrophilic contact lens with a water content of 38% to 85% is brought into contact with the lacrimal fluid, the contact lens absorbing the lacrimal fluid which is then extracted by immersing the contact lens in an extractive solution with a 0.8% to 4% concentration of salts, at least one of which is sodium chloride. The extraction takes place at a temperature of 20° to 24° C., and lasts up to two hours during which the extractive solution is stirred or agitated.

13 Claims, No Drawings

METHOD FOR OBTAINING LACRIMAL FLUID

BACKGROUND OF THE INVENTION

The present invention relates to a method for obtaining lacrimal fluid by means of contact lenses, as well as to the use of suitable contact lenses in carrying out the method of the invention.

Knowledge about the composition of the lacrimal fluid, i.e. of mostly unchanged lacrimal fluid as produced by the cornea of the eye during resting secretion, can be gained only through analytical study of lacrimal fluid extracted from the eye. In practice, this knowledge has significant bearing on such matters as whether a patient should be advised to wear contact lenses, or what a particular patient's tolerance is for various types of contact lenses. It is in fact impossible to prevent the inserted contact lens from affecting normal lacrimal circulation on the corneal surface. Since the lacrimal fluid serves, among other things, as carrier of nutrients and active substances, which it supplies to the cornea, a disturbance of the lacrimal fluid's circulation can also lead to an undesirable impairment of the corneal metabolism with correspondingly unfavorable side effects. Based on the characteristic composition of the lacrimal fluid, the experienced opthalmologist or optician is able to select from among the various types of contact lenses the one that the wearer can be expected to tolerate. In the case of patients who have been wearing contact lenses for some time, it is possible, in addition, based on the composition of the lacrimal fluid, to draw certain conclusions regarding a threatening or already existing disturbance of the corneal metabolism.

In order to be able to carry out such studies, one needs a method for the collection of lacrimal fluid that is as simple as possible but effective. The methods known up to now for the collection of lacrimal fluid can practically not be carried out without irritating the eye. In the Schirmer test, for example, a narrow strip of filter paper is laid on the cornea or in the inferior conjunctival fornix of the eye to determine the rate of tear production. The person being tested does not find this procedure to be a pleasant one since it is impossible to insert the filter paper strips without causing a slight burning sensation in the eye. The unavoidable eye irritation causes an increased production of lacrimal fluid, the composition of which differs decidedly, however, from that of normal, so-called resting secretion since most of the additionally produced lacrimal fluid is caused by a heightened stimulation of the main lacrimal gland whereby the proportion of the aqueous component rises simultaneously with a change in the tonicity and a shift of the pH level in the direction of basicity.

Even a pipette cannot be used to draw lacrimal fluid from the inner canthus without eye irritation, no matter how carefully handled. In this case, also, there is undesirably enhanced production of lacrimal fluid with the unavoidable attendant change in it composition.

Other attempts to stimulate the production of lacrimal fluid, for example, the careful massaging of the eye or the use of certain stimuli such as the stimulus of freshly peeled onion, do not obviate the above problems either, not to mention the fact that such treatments are not exactly pleasant for the patient.

Thus, these known methods can only obtain lacrimal fluid that, owing to the irritation of the eye, contains an excess of the aqueous component and whose composition therefore differs markedly from an undiluted lacrimal fluid, i.e. from a resting secretion. It is thus not possible, with known methods, to obtain pure resting secretion in which the composition of the natural lacrimal fluid can be measured.

The object of the present invention is therefore to create a method which avoids the drawbacks resulting from the known methods for obtaining lacrimal fluid and which, in addition, allows for a markedly higher yield of lacrimal fluid in one single operation.

SUMMARY OF THE INVENTION

There has now been discovered a method for obtaining lacrimal fluid, characterized in that a hydrophilic contact lens, with a water content of 38% to 85%, is brought into contact with a lacrimal fluid, the contact lens containing the lacrimal fluid is treated for a period of 30 minutes to 2 hours at a temperature of 20° to 24° C., with an extractive solution with a 0.8% to 4% concentration of salts, at least one of which is sodium chloride, as a result of which the lacrimal fluid is extracted from the contact lens.

It was a surprising discovery to find that the known soft hydrophilic contact lenses not only are capable of absorbing in a relatively short time a considerable quantity of lacrimal fluid, including the substances dissolved in it, but that they will also give up this lacrimal fluid in a relatively short time to an appropriate extractive solution. Since the contact lenses cause practically no appreciable eye irritation, they also do not cause an increased production by the main lacrimal gland of a more watery, low-protein secretion, nor do they cause the attendant dilution that is undesirable because of its altering effect. In this manner, the use of contact lenses—a treatment that is gentle to the patient—makes it possible to obtain lacrimal fluid in its natural state. Thus the method of the invention creates the basis for determining the exact composition of the lacrimal fluid in the form of resting secretion.

DETAILED DESCRIPTION OF THE INVENTION

The soft hydrophilic contact lenses used in the method of the present invention are known of themselves and are available on the commercial market. These contact lenses are characterized by a high water content of 30% to 85% and by the particular softness of the material. The absorption capacity of hydrophilic contact lenses for lacrimal fluid rises generally with their water content, which is why hydrophilic contact lenses with a water content of 65% to 85% are preferred. Furthermore, the usability of the hydrophilic contact lenses for the method of the invention depends on the composition of the polymers used. Hydrophilic contact lenses made of methyl methacrylate/vinyl pyrrolidone (abbreviated: MMA/VP copolymer) have proven to be advantageous and therefore constitute a preferred embodiment, e.g. those that have an MMA/VP ratio of 30:70 and a water content of 70%. Another preferred embodiment are hydrophilic lenses made of 2-hydroxy ethyl methacrylate/vinyl pyrrolidone copolymers (abbreviated: HEMA/VP copolymers), since they present an exceptionally high absorption capacity for lacrimal fluids. Particularly advantageous, for example, are copolymers of HEMA/VP with a weight ratio of 50:50 and a water content of 68% or with a weight ratio of 10:90 and a water content of 85%.

The contact lenses usually weigh about 50 to 70 mg.

The tested person has to wear the contact lens for only a relatively short time to absorb the lacrimal fluid since the balance between the quantities of absorbed and of released lacrimal fluid (the so-called equilibration) is attained in the contact lens within a period of 30 minutes to 2 hours.

Once the equilibration of the contact lens by the lacrimal fluid is achieved, but possibly even sooner, the contact lens is removed from the eye and—after short drying with filter paper, if needed—is placed in a suitable extractive solution, which has a 0.8 to 4% content of salts, of which one at least is sodium chloride. The extractive solution is maintained at a temperature of 20° to 24° C. To speed up the extraction, the solution is stirred or agitated, so that the extraction can generally be completed within 30 minutes, or within 2 hours in more difficult cases.

The contact lens having released its lacrimal fluid, is removed from the solution, and the solution is then subjected to analytical tests to determine the substances and active matters contained in the lacrimal fluid. The analytical tests are known of themselves and generally apply micro-analytical processes such as the biuret reaction for measuring the protein content of the lacrimal fluid, or the selective lysozyme determination in accordance with Selsted and Martinez.

The effectiveness of the method of the invention depends not only on the quality of the soft hydrophilic lens used but also on the type and composition of the extractive solution. In a particularly simple, preferred embodiment of the method of the invention, the extractive solution contains 0.85% sodium chloride, which gives it about the same tonicity as that of the lacrimal fluid. Such an extractive solution is preferred because it is particularly beneficial for the contact lens, and because there is no reason to fear swelling or shrinking of the contact lens, even after prolonged treatment. Such an extractive solution is preferably neutral, i.e. with a pH of about 7.

In some cases, however, it may be preferable to raise, or lower, the pH in order to improve the extraction of the lacrimal fluid, or of certain substances contained in it, from the contact lens. In another preferred embodiment of the method of the invention, therefore, an extractive solution is used whose pH has been raised to a level of 8 to 11 by a base such as sodium or ammonium hydroxide. On the other hand, an extractive solution can be used in a further preferred embodiment, whose pH has been lowered to a level of 6 to 2.5 by means of a diluted liquid acid, such as acetic acid, propionic acid, etc.

In order to achieve as rapid and complete an extraction as possible, particularly of the protein components of the lacrimal fluid, it may also be advantageous to change the polarity of the extractive solution, e.g. by using preferably an extractive solution with a content of 1% to 10% of dioxan or perferably, again, with a content of 5% to 50% ethylene glycol.

It can also be advantageous for the extractive solution to contain so-called "hydrogen bond breakers" for the effective extraction of proteins. This is done preferably by the admixture of urea or guanidine hydrochloride, the former preferably in the form of an eight-molar solution, the latter in that of a six-molar solution.

Finally, those salts can also be admixed in the extractive solution which reduce the hydrophobic interaction between contact lens and protein and thereby also facilitate the extraction of the proteins. These include solutions of sodium rhodanide, trichloroacetic acid or sodium iodide, e.g. in three-molar solution.

In no case, however, should the total salt content of the extractive solution exceed 4% by weight.

In a preferred embodiment, hydrophilic contact lenses with a water content of 38% to 85% are used in the method of the invention for obtaining lacrimal fluid. Soft hydrophilic contact lenses with the above water content are basically suited for the purpose of the invention; it has been found, however, that hydrophilic contact lenses whose water content is closer to the upper limit of the range indicated and/or that are made of a material with larger pores, with a pore diameter in the order of magnitude of 5 nm, mostly have a considerably higher absorption capacity for lacrimal fluid and, in particular, for the larger molecules dissolved in the lacrimal fluid. This applies especially to hydrophilic contact lenses with a water content of about 70% and, to an even greater degree, to hydrophilic contact lenses made of HEMA/VP copolymers with a water content of 70%, for which reason the use of such types of contact lenses is greatly preferred.

One advantage of the present invention is that, by contrast with the methods presently known and applied for obtaining lacrimal fluid, the method of the invention permits a generally non-irritating collection of lacrimal fluid from the eye. It is thereby possible to prevent the main lacrimal gland from producing additional lacrimal fluid, which, compared to resting secretion, has an excess of aqueous component and presents a pH shift in the direction of basicity, as well as reduced tonicity. With respect to properties and composition, the lacrimal fluid obtained by the method of the invention thus corresponds in wide measure to the normal lacrimal fluid, i.e. the so-called resting secretion. By means of the present invention it is, therefore, possible to eliminate the causes of considerable error in determining the composition of normal lacrimal fluid.

A further advantage of the invention is that greater amounts of lacrimal fluid can be obtained than is possible with the known methods. By pipetting, for example, it is possible to obtain only about 5 to 6 $\mu l$ of lacrimal fluid, while causing irritation of the eye, i.e. heightened stimulation of the main lacrimal gland, with its attendant adverse consequences. With the method of the invention, on the contrary, using a hydrophilic contact lens, for example, of HEMA/VP copolymer, made of 60% 2-hydroxy ethyl methacrylate and 40% vinyl pyrrolidone, with a water content of 65%, weighing about 50 mg, it is possible to obtain about 25 $\mu l$ of lacrimal fluid, i.e. five times as much as by pipetting. Such a quantity is naturally easier to handle during micro-analysis and makes for more reliable findings. With other contact lenses, such as those made of HEMA/VP copolymers with a water content of approximately 70% to 85%, even larger amounts of lacrimal fluid can be obtained.

The invention is explained in greater detail by means of the following example.

EXAMPLE

A contact lens of HEMA/VP copolymer, made of 60% HEMA and 40% VP, with a water content of 65%, was placed on the left eye of a test person. During the 30 minutes the contact lens remained on the eye, the patient experienced no noticeable eye irritation. Nor was any flow of lacrimal fluid observed beyond the normal amount. Thirty minutes after insertion, the contact lens was removed, briefly dried with filter paper and placed in 0.2 ml of a 0.85% sodium chloride solution maintained at 21° C. Extraction of the lacrimal fluid from the contact lens was completed in 30 minutes, the solution being continuously agitated. The contact lens was then removed from the extractive solution.

The extractive solution containing the lacrimal fluid was then tested by means of the biuret reaction for total protein concentration in the lacrimal fluid. The biuret reagent consisted of 0.6 g of potassium sodium tartrate dissolved in 300 ml of a sodium chloride solution to which 1.5 g of $CuSO_4 5H_2O$ and 1 g of potassium iodide had been added. This solution was brought to the 1 liter level with water containing no carbon dioxide.

Eight tenths ml of the biuret reagent were added to the extractive solution and the mixture was allowed to stand at room temperature. After 30 minutes, the solution was measured in the photometer under 540 nm against a blank test value. The measurement can be effected by visual color comparison.

Evaluation was carried out by means of a previously prepared calibration curve. The latter had been established as follows: contact lenses made of HEMA/VP copolymer (60% HEMA, 40% VP), with a water content of 65%, were agitated for 30 minutes, each, in 0.85% sodium chloride solutions containing dissolved albumin in graduated concentrations of 0.1% to 1.5%, in the course of which the contact lenses absorbed a certain amount of the albuminous solutions corresponding approximately to the equilibrium quantity. This was followed by extraction from each contact lens in 0.2 ml of a 0.85% sodium chloride solution agitated for 30 minutes. Then the contact lens was removed from the solution and the amount of albumin in the solution was measured photometrically under 540 nm by means of the biuret reaction. The measured absorbance values were plotted graphically against albumin concentration.

The calibration curve thus obtained revealed a total protein content of 0.75% (w/v) in the lacrimal fluid being tested.

The visual evaluation was carried out as follows: for comparison, a contact lens of the same type and dimension as the one used for the test was treated with a 0.7% albumin solution in the same manner as described above. The 0.7% albumin solution corresponds essentially to the total protein concentration usually found in a "normal" lacrimal fluid, i.e. in the resting secretion. After removal of the contact lenses and completion of the biuret reaction in the resulting extractive solutions, the color intensity was determined by visual comparison. The result was in good agreement with that of the absorbance measurement.

In lieu of the total protein content, one can also measure in the extractive solution containing the lacrimal fluid the latter's lysozyme content. Lysozyme is an important enzyme capable of regulating the bacterial flora in the lacrimal fluid and of destroying dangerous germs. For the purpose of advising persons who want to wear contact lenses, it is therefore particularly important to know the condition of the lacrimal fluid, particularly with regard to lysozyme content.

The determination of the lysozyme content in the extractive solution containing the lacrimal fluid is carried out selectively according to the method of M. E. Selsted and R. J. Martinez, Analytical Biochemistry, No. 109, pp. 67–70, 1980. The substrate used in this method is a suspension of deactivated Micrococcus lysodeicticus cells.

The principle of this method is that the lacrimal fluid in a contact lens is extracted by an extractive solution containing micrococcus cells of the above-cited type. Because of the suspension, this extractive solution is very cloudy. After the extraction, the cloudiness is reduced more or less, depending on the amount of lysozyme present in the lacrimal fluid. This change also modifies the absorbance, so that the lysozyme concentration can thus be determined by means of photometric measurements under 540 nm.

Tests were carried out accordingly on 16 different persons. The findings of these tests are summarized in the following table. It is readily seen that the various contact lens materials differ markedly in regard to absorption capacity for lacrimal fluid or in regard to lysozyme content.

The absorption capacity of contact lenses made of HEMA/VP copolymers is particularly satisfactory, and contact lenses made of MMA/VP copolymers also yield good results. By contrast, the hard contact lens material cellulose acetate butyrate is unsuitable for the absorption of lacrimal fluid.

| | | Measurement of the Lysozyme Content in Lacrimal Fluids Extracted from Contact Lenses | | |
|---|---|---|---|---|
| | | Lysozyme Content of Contact Lenses (CL) | | Weight of the Contact Lenses |
| Test No. | Contact Lens Material | ($\mu$g/mg wet CL) | ($\mu$g/CL) | (mg) |
| 1 | MMA/VP* | 0.24 | 6.7 | 27.57 |
| 2 | MMA/VP | 0.32 | 11.6 | 36.79 |
| 3 | MMA/VP | 0.56 | 26.1 | 46.79 |
| 4 | MMA/VP | 0.55 | 24.5 | 44.93 |
| 5 | MMA/VP | 0.30 | 11.5 | 37.91 |
| 6 | HEMA/VP** | 38.96 | 1909.1 | 49.00 |
| 7 | HEMA/VP | 49.11 | 2312.0 | 47.08 |
| 8 | HEMA/VP | 45.59 | 1885.5 | 41.35 |
| 9 | HEMA/VP | 7.87 | 475.3 | 60.38 |
| 10 | HEMA/VP | 8.64 | 475.4 | 55.00 |
| 11 | HEMA/VP | 13.28 | 925.7 | 69.65 |
| 12 | HEMA/VP | 9.85 | 675.2 | 68.56 |
| 13 | HEMA/VP | 12.83 | 850.2 | 66.27 |
| 14 | HEMA/VP | 6.09 | 325.3 | 53.37 |
| 15 | PHEMA*** | 0.18 | 6.6 | 37.39 |
| 16 | CAB**** | 0.09 | 1.6 | 18.35 |

*MMA/VP = methyl methacrylate/vinyl pyrrolidone copolymer (approx. 70% $H_2O$)
**HEMA/VP = 2-hydroxyethyl methacrylate/vinyl pyrrolidone copolymer
***PHEMA — poly-2-hydroxyethyl methacrylate (approx. 40% $H_2O$)
****CAB = cellulose acetate butyrate (= hard contact lens material)

All percentages recited herein are by weight unless noted otherwise.

What is claimed is:

1. A method for obtaining lacrimal fluid comprising contacting a hydrophilic contact lens with a water content of 38% to 85% with a lacrimal fluid, permitting the contact lens to absorb the lacrimal fluid, thereafter treating the contact lens containing the lacrimal fluid for a period of 30 minutes to 2 hours at a temperature of 20° to 24° C. with an extractive solution that has a 0.8% to 4% concentration of salts, at least one of which is sodium chloride, resulting in the extraction of the lacrimal fluid from the contact lens.

2. A method according to claim 1 wherein a hydrophilic contact lens with a water content of 65% to 85% is used.

3. A method according to claim 1 wherein a hydrophilic contact lens made of a methyl methacrylate/vinyl pyrrolidone copolymer is used.

4. A method according to claim 1 wherein a hydrophilic contact lens made of a 2-hydroxyethyl methacrylate/vinyl pyrrolidone copolymer is used.

5. A method according to claim 1 wherein the hydrophilic contact lens is brought into contact with the lacrimal fluid for a period of 30 minutes to 2 hours.

6. A method according to claim 1 wherein an extractive solution is used, the pH of which is about 7.

7. A method according to claim 1 wherein an extractive solution is used, the pH of which is set to a level of about 8 to 11 by means of a base.

8. A method according to claim 1 wherein an extractive solution is used, the pH of which is set to a level of 6 to 2.5 by means of a diluted volatile acid.

9. A method according to claim 1 wherein an extractive solution with a 0.85% sodium chloride content is used.

10. A method according to claim 1 wherein an extractive solution with a content of 1% to 10% dioxan content is used.

11. A method according to claim 1 wherein an extractive solution with a content of 5% to 50% ethylene glycol is used.

12. A method according to claim 1 wherein an extractive solution with a content of urea or guanidine hydrochloride is used.

13. A method according to claim 1 wherein the solution containing lacrimal fluid is subjected to analytical tests.

* * * * *